United States Patent [19]

Toda et al.

[11] Patent Number: 4,467,102
[45] Date of Patent: Aug. 21, 1984

[54] OPTICALLY ACTIVE PROPARGYL ALCOHOL DERIVATIVE AND A METHOD FOR PREPARATION OF THE SAME

[75] Inventors: Fumio Toda, Ehime; Koichi Tanaka, Matsuyama, both of Japan

[73] Assignee: Ube Industries, Ltd., Yamaguchi, Japan

[21] Appl. No.: 553,644

[22] Filed: Nov. 21, 1983

Related U.S. Application Data

[63] Continuation of Ser. No. 383,580, Jun. 1, 1982.

[30] Foreign Application Priority Data

Mar. 4, 1982 [JP] Japan ................................. 57-33011

[51] Int. Cl.³ .......................................... C07D 333/00
[52] U.S. Cl. ...................................... 549/78; 568/809; 568/812; 568/813
[58] Field of Search .................. 549/78; 568/809, 812, 568/813

[56] References Cited

PUBLICATIONS

Eliel, Sterochem of Carbon Comp., 1962, pp. 48–57.

Primary Examiner—Alan Siegel
Attorney, Agent, or Firm—Finnegan, Henderson, Farabow, Garrett & Dunner

[57] ABSTRACT

An optically active propargyl alcohol derivative of the formula (I)

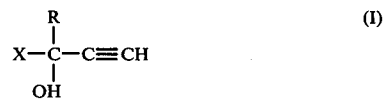

wherein X=phenyl or thienyl and R=lower alkyl, halogenated methyl, phenyl or substituted phenyl having at least one lower alkyl radical and or halogen atom, is prepared by contacting a racemic modification of l- and d-isomers of the formula (I) with l-brucine in an organic solvent, by separating the resultant deposited diastereomer from a solution containing the resultant other diastereomer in the organic solvent, by decomposing each diastereomer with an aqueous mineral acid solution in the presence of an organic solvent capable of dissolving the corresponding optically active isomer dissociated from the diastereomer and incompatible with water so as to allow the optically active isomer to be dissolved in the water-incompatible organic solvent, and by recovering the optically active isomer from the solution thereof.

16 Claims, No Drawings

OPTICALLY ACTIVE PROPARGYL ALCOHOL DERIVATIVE AND A METHOD FOR PREPARATION OF THE SAME

This is a continuation of application Ser. No. 383,580, filed June 1, 1982.

FIELD OF THE INVENTION

The present invention relates to new propargyl alcohol derivatives having optical activity and to a method for preparation of the same by means of racemic resolution.

BACKGROUND OF THE INVENTION

It is known that usually the resolution of a racemic modification is carried out by means of a diastereomer method in which an optically active resolving agent is used. However, the type of racemic modification which is capable of forming the corresponding diastereomer is limited depending on the type of resolving agent to be used. Therefore, it is important to provide a new type of optically active resolving agent which is effective for resolving various racemic modifications.

SUMMARY OF THE INVENTION

An object of the present invention is to provide an optically active propargyl alcohol derivative which is useful as a new type of optically active resolving agent and a method for preparation of the same by means of racemic resolution.

Another object of the present invention is to provide an optically active propargyl alcohol derivative which is useful as a starting material for various medicines, agricultural chemicals, and perfumes and a method for preparation of the same by means of racemic resolution.

The above-mentioned optically active propargyl alcohol derivative, by which the above-mentioned objects can be attained, is of the formula (I):

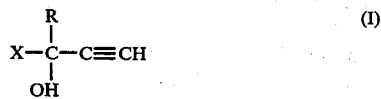

wherein X represents a member selected from the group consisting of phenyl and thienyl radicals and R represents a member selected from the group consisting of lower alkyl radicals, halogenated methyl radicals, a phenyl radical, and substituted phenyl radicals each having at least one substituent selected from the group consisting of lower alkyl radicals and halogen atoms.

The method of the present invention, by which the above-mentioned objects can also be attained, comprises the steps of:

bringing a racemic modification of l- and d-propargyl alcohol derivatives of the formula (I) into contact with l-brucine in an organic solvent, whereby a mixture of diastereomers of l-brucine with an l-isomer and a d-isomer of a propargyl alcohol derivative of the formula (I) is produced and one of the diastereomers deposits from the organic solvent and the other one is dissolved in the organic solvent;

separating the deposited diastereomer from the solution containing the other diastereomer;

decomposing each of the diastereomers to dissociate l-brucine from the corresponding optically active isomer of the l-phenyl propargyl alcohol derivative of the formula (I) in the presence of an organic solvent which is capable of dissolving the corresponding optically active isomer and is incompatible with water by bringing each diastereomer into contact with an aqueous solution of a mineral acid; whereby the resultant optically active isomer is dissolved in the water-incompatible organic solvent and the dissociated l-brucine is dissolved in the aqueous mineral acid solution; and isolating the resultant optically active isomer from the decomposition mixture.

DETAILED DESCRIPTION OF THE INVENTION

The optically active propargyl alcohol derivative of the present invention is of the formula (I):

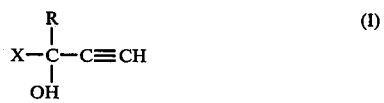

wherein X represents a member selected from the group consisting of phenyl and thienyl radicals and R represents a member selected from the group consisting of lower alkyl radicals, halogenated methyl radicals, a phenyl radical and substituted phenyl radicals each having at least one substituent selected from the group consisting of lower alkyl radicals and halogen atoms.

In the formula (I), the lower alkyl radical represented by R may have 1 to 6 carbon atoms and the halogenated methyl radical represented by R may be selected from the group consisting of chlorinated methyl radicals, fluorinated methyl radicals and brominated methyl radicals. Also, in the substituted phenyl radical represented by R in the formula (I), the lower alkyl radicals may have 1 to 3 carbon atoms and the halogen atom may be selected from chlorine, fluorine and bromine atoms.

That is, the optically active propargyl alcohol derivatives include:
1-tert-butyl-1-phenyl propargyl alcohol,
1-tert-amyl-1-phenyl propargyl alcohol,
1-sec-butyl-1-phenyl propargyl alcohol,
1-o-tolyl-1-phenyl propargyl alcohol,
1-n-butyl-1-phenyl propargyl alcohol,
1-o-chlorophenyl-1-phenyl propargyl alcohol,
1-isopropyl-1-phenyl propargyl alcohol,
1-p-tolyl-1-phenyl propargyl alcohol,
1-n-propyl-1-phenyl propargyl alcohol,
1-o-fluorophenyl-1-phenyl propargyl alcohol,
1-ethyl-1-phenyl propargyl alcohol,
1-monobromomethyl-1-phenyl propargyl alcohol,
1-o-bromophenyl-1-phenyl propargyl alcohol,
1-trifluoromethyl-1-phenyl propargyl alcohol,
1-m-chlorophenyl-1-phenyl propargyl alcohol,
1-(2,4-dimethylphenyl)-1-phenyl propargyl alcohol,
1-methyl-1-phenyl propargyl alcohol,
1-trichloromethyl-1-phenyl propargyl alcohol,
1-dichloromethyl-1-phenyl propargyl alcohol,
1-monochloromethyl-1-phenyl propargyl alcohol,
1-n-propyl-1-thienyl propargyl alcohol,
1-isopropyl-1-thienyl propargyl alcohol,
1-n-butyl-1-thienyl propargyl alcohol and
1-n-amyl-1-thienyl propargyl alcohol.

In the method of the present invention for the preparation of the optically active propargyl alcohol derivative of the formula (I), a racemic modification of l- and d-propargyl alcohol derivatives of the formula (I) is brought into contact with a resolving agent consisting of l-brucine dissolved in an organic solvent.

The racemic modification of optically active l- and d-propargyl alcohol derivatives of the formula (I) can be prepared by reacting a ketone compound of the formula (II):

wherein X and R are the same as defined hereinbefore with sodium acetylide in a liquid ammonia and by hydrolyzing the resultant sodium salt of the racemic modification of l- and d-propargyl alcohol derivatives of the formula (I).

The above-mentioned reaction is carried out in a liquid ammonia under atmospheric pressure at an ambient temperature in accordance with the following formula:

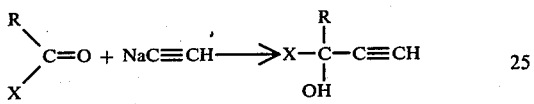

The reaction mixture is left standing at the ambient temperature while allowing the liquid ammonia to evaporate.

The resultant sodium salt of the racemic modification of the l- and d-isomers is hydrolyzed to provide the racemic modification of the l- and d-isomers.

The sodium acetylide can be prepared by blowing a stream of acetylene gas into a solution of sodium amide in liquid ammonia. Therefore, preparation of the sodium salt of the racemic modification may be carried out by adding the ketone compound of the formula (II) to the reaction mixture of the sodium amide solution in liquid ammonia while blowing acetylene gas into the mixture.

l-brucine naturally exists in the seeds of plants of the Mazin family, for example, Strychnos nux-vomica L and S ignatti Berg, and is of the formula:

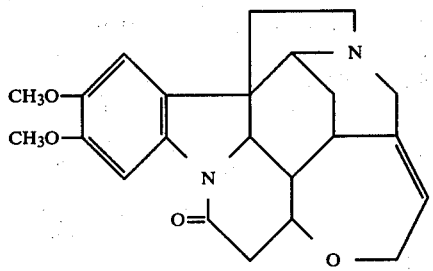

The organic solvent is capable of dissolving l-brucine and may be selected from the group consisting of acetone, methyl alcohol and ethyl acetate.

When the racemic modification is brought into contact with l-brucine, the racemic modification is converted into a mixture of diastereomers of l-brucine with l- and d-isomers. One of the resultant diastereomers deposits from the organic solvent while the other one is dissolved in the organic solvent.

In the above-mentioned procedure for preparation of the diastereomer mixture, a predetermined amount of l-brucine is dissolved in an amount of the organic solvent necessary for completely dissolving the amount of l-brucine or in an amount of the organic solvent slightly in excess of the above-mentioned necessary amount. The racemic modification of the l- and d-isomers is added to the l-brucine solution. The molar amount of the racemic modification is substantially equivalent to the molar amount of l-brucine used.

Contact of the racemic modification with the l-brucine solution is carried out, preferably at a temperature of from 10° to 50° C., for a period of time necessary for completing the formation of diastereomers, for example, 10 to 30 hours at room temperature.

The resultant product is a mixture of a diastereomer of l-brucine with an l-isomer and a diastereomer of l-brucine with a d-isomer. One of the diastereomers is insoluble in the organic solvent and deposits from the organic solvent, and other diastereomer is soluble in the organic solvent and, therefore, is dissolved in the organic solvent.

In the method of the present invention, the deposited diastereomer is separated from the solution containing the other diastereomer in the organic solvent by a usual separating procedure, for example, filtration or centrifugal separation.

The type of deposited diastereomer is an alternative to the diastereomers of l-brucine with l- and d-isomers, depending on the type of isomers and the type of organic solvent used. That is, the deposited diastereomer is sometimes a diastereomer of an optically active l-isomer and sometimes a diastereomer of an optically active d-isomer.

In the method of the present invention, each diastereomer is subjected to a decomposition procedure by which l-brucine and the optically active l- or d-isomer are dissociated from each other.

The decomposition procedure is carried out by bringing the diastereomer into contact with an aqueous solution of a mineral acid in the presence of an organic solvent which is capable of dissolving the resultant optically active isomer and is incompatible with water. By this decomposition procedure, the dissociated optically active isomer is dissolved in the water-incompatible organic solvent and the dissociated l-brucine is dissolved in the aqueous mineral acid solution.

Before the decomposition procedure is carried out, the diastereomer which has deposited from the organic solvent is separated from the organic solvent, and the separated diastereomer is dissolved in the water-incompatible organic solvent. Thereafter, the solution is subjected to the decomposition procedure.

However, in the case of the diastereomer which has been dissolved in the organic solvent, the solution of the diastereomer is separated from the deposited diastereomer and is mixed with the water-incompatible organic solvent. The mixture is then subjected to the decomposition procedure. In this case, the amount of the water-incompatible organic solvent to be mixed with the solution of the diastereomer should be sufficient to completely dissolve the resultant optically active isomer in the decomposition procedure. Before the above-mentioned mixing is carried out, the solution of the diastereomer may be concentrated by evaporating at least a portion of the organic solvent from the solution.

The water-incompatible organic solvent, which is capable of dissolving the resultant optically active isomer in the decomposition procedure, may be selected from the group consisting of benzene, toluene, and xylene.

The mineral acid usable for the decomposition procedure may comprise at least one member selected from the group consisting of hydrochloric acid, sulfuric acid, and nitric acid.

The concentration of the mineral acid in the aqueous solution thereof is not limited to a special range of values as long as the aqueous mineral acid solution is effective for decomposing the diastereomer. However, usually, it is preferable that the decomposing procedure be carried out at a mineral acid concentration of from 1 to 30% and at a pH of from 1 to 4.

Also, it is preferable that contact of the diastereomer with the aqueous mineral acid solution be carried out at a temperature of from 10° to 50° C. for a period of time necessary for completing the decomposition; for example, from 5 to 60 minutes.

By means of the above-mentioned decomposition procedure, the diastereomer is decomposed to form the dissociated corresponding optically active l- or d-isomer and the dissociated l-brucine, and the dissociated optically active isomer is dissolved in the water-incompatible organic solvent while the dissociated l-brucine is dissolved in the aqueous mineral acid solution. Therefore, the solution phase of the optical active isomer in the water-incompatible organic solvent is separated from the aqueous solution phase of l-brucine.

The solution of the optically active isomer is separated from the aqueous l-brucine solution. The optically active isomer can be isolated from the solution thereof by eliminating the water-incompatible organic solvent from the solution by means of evaporation.

The aqueous solution of l-brucine and the mineral acid is added to an alkali aqueous solution in order to allow l-brucine to deposit from the aqueous solution. The deposited l-brucine is separated from the aqueous solution, and the recovered l-brucine can be recycled to the optically active isomer-producing process.

The optically active propargyl alcohol derivatives of the present invention represented by the formula (I) are useful not only as resolving agents for various racemic modifications of optically active compounds, for example, sparteine lactams and lactones, but also as starting materials for various medicines, agricultural chemicals, and perfumes, for example, atrolactamide, mandelonitrile and cyanohydrines.

The following specific examples are presented for the purpose of clarifying the present invention. However, it should be understood that these are intended only to be examples of the present invention and are not intended to limit the present invention in any way.

EXAMPLE 1

Preparation of Racemic Modification

A liquid ammonia in an amount of 1500 ml was cooled to a temperature of approximately −65° C., and 80 g of sodiumamide was added to the cooled liquid ammonia. Next, while the temperature of the sodiumamide-ammonia mixture was maintained at the above-mentioned level, acetylene gas was introduced into the mixture at a flow rate of 1000 ml/min for 120 minutes under atmospheric pressure. A solution of sodium acetylide in the liquid ammonia was obtained. The sodium acetylide solution was mixed with 500 g of tert-butyl phenyl ketone. The reaction mixture was kept at a temperature of approximately −65° C. for 120 minutes and thereafter was let stand at the ambient temperature so as to allow the liquid ammonia to evaporate. The residue consisting of sodium salt of 1-tert-butyl-1-phenyl propargyl alcohol racemic modification was subjected to hydrolysis at room temperature, and the product of hydrolysis was subjected to distillation. A racemic modification of 1-tert-butyl-1-phenyl propargyl alcohol having a boiling point of 112° C. under a pressure of 8 mmHg was obtained in an amount of 505 g.

Racemic Resolution

A solution of 28 g of l-brucine in 300 ml of acetone was mixed with 13 g of the racemic modification of 1-tert-butyl-1-phenyl propargyl alcohol. The resultant solution was let stand at room temperature for 24 hours while colorless, prism-shaped crystals were allowed to precipitate from the solution.

The colorless, prism-shaped crystals which consisted of a diastereomer of l-brucine with d-1-tert-butyl-1-phenyl propargyl alcohol were collected from the solution by means of filtration. The amount of the collected diastereomer of the d-isomer was 20.1 g. The diastereomer of the d-isomer was dissolved in 30 ml of benzene. The solution was mixed with 30 ml of a diluted hydrochloric acid-aqueous solution (concentration: 100 g/l). The mixture was stirred at room temperature for 5 minutes so as to decompose the diastereomer. Thereafter, the mixture was let stand at room temperature until the benzene solution phase containing the dissociated d-1-tert-butyl-1-phenyl propargyl alcohol was completely separated from the hydrochloric acid-aqueous solution phase containing the dissociated l-brucine. The benzene solution was collected from the mixture by means of filtration and then was subjected to a distillation procedure. The resultant product consisted of 6.5 g of d-1-tert-butyl-1-phenyl propargyl alcohol.

The residual solution containing a diastereomer of l-l-brucine with l-1-tert-butyl-1-phenyl propargyl alcohol in acetone was mixed with 30 ml of benzene and then with 30 ml of the same aqueous solution of 100 g/l of hydrochloric acid as that described above. The mixture was stirred at room temperature for 5 minutes. Thereafter, the mixture was let stand at room temperature until a phase of the benzene solution containing l-1-tert-butyl-1-phenyl propargyl alcohol was separated from a phase of the aqueous solution containing l-brucine. The l-isomer was isolated in an amount of 6.8 g from the benzene solution in the same manner as that mentioned above.

The optical rotation properties of the d- and l-isomers in methyl alcohol are indicated in Table 1.

EXAMPLE 2 THROUGH 24

In each of the Examples 2 through 24, the same racemic modification-producing procedures as those described in Example 1 were carried out except that 500 g of tert-butyl phenylketone was replaced by 500 g of the type of compound indicated in Table 1.

The resultant racemic modification was obtained in the amount indicated in Table 1 and exhibited the boiling or melting point indicated in Table 1.

The same racemic resolution procedures as those mentioned in Example 1 were carried out except that the type and amount of the deposited diastereomer were as indicated in Table 1 and the amounts of the resultant l- and d-isomers were as indicated in Table 1.

The optical rotation properties of the l- and d-isomers in methyl alcohol are indicated in Table 1.

TABLE 1

| Example No. | Starting ketone compound Type | Starting ketone Amount used (g) | Racemic modification Amount obtained (g) | Racemic modification Boiling or melting point | Amount used (g) | Deposited diastereomer Type of isomer | Deposited diastereomer Amount obtained (%) | Name | Formula | Optically active isomer d-isomer $[\alpha]_D^{25}$ (methanol) | d-isomer Amount obtained (g) | l-isomer $[\alpha]_D^{25}$ (methanol) | l-isomer Amount obtained (g) |
|---|---|---|---|---|---|---|---|---|---|---|---|---|---|
| 1 | tert-butyl-phenyl ketone | 500 | 505 | b.p. = 112° C. (8mmHg) | 13.0 | d-isomer | 20.1 | 1-tert-butyl-1-phenyl propargyl alcohol | (structure) | +12.0° (C = 0.36) | 6.5 | −11.8° (C = 0.35) | 6.8 |
| 2 | tert-amyl-phenyl ketone | 500 | 510 | b.p. = 109° C. (2mmHg) | 9.9 | d-isomer | 14.3 | 1-tert-amyl-1-phenyl propargyl alcohol | (structure) | +10.5° (C = 0.26) | 4.8 | −8.9° (C = 0.24) | 5.0 |
| 3 | sec-butyl-phenyl ketone | 500 | 520 | b.p. = 104° C. (10mmHg) | 11.3 | l-isomer | 17.2 | 1-sec-butyl-1-phenyl propargyl alcohol | (structure) | +8.7° (C = 0.36) | 5.1 | −8.5° (C = 0.34) | 5.6 |
| 4 | n-butyl-phenyl ketone | 500 | 520 | b.p. = 99° C. (4mmHg) | 10.8 | d-isomer | 16.4 | 1-n-butyl-1-phenyl propargyl alcohol | (structure) | +7.9° (C = 0.23) | 5.3 | — | — |
| 5 | isopropyl-phenyl ketone | 500 | 515 | b.p. = 74° C. (2.5mmHg) | 15.3 | d-isomer | 24.5 | 1-isopropyl-1-phenyl propargyl alcohol | (structure) | +1.1° (C = 0.27) | 7.5 | −1.5° (C = 3.0) | 7.1 |

TABLE 1-continued

| | Starting ketone compound | | Racemic modification | | Deposited diastereomer | | Optically active isomer | | | | |
|---|---|---|---|---|---|---|---|---|---|---|---|
| | | | | | | | | d-isomer | | l-isomer | |
| Example No. | Type | Amount used (g) | Amount obtained (g) | Boiling or melting point | Amount used (g) | Type of isomer | Amount obtained (%) | Name | Formula | $[\alpha]_D^{25}$ (methanol) | Amount obtained (g) | $[\alpha]_D^{25}$ (methanol) | Amount obtained (g) |
| 6 | n-propyl-phenyl ketone | 500 | 500 | b.p. = 106° C. (5mmHg) | 26.0 | d-isomer | 41.6 | 1-n-propyl-1-phenyl propargyl alcohol | (CH₃—CH₂—CH₂—C(OH)(C≡CH)—C₆H₅) | +4.5° (C = 0.57) | 12.7 | −4.8° (C = 0.56) | 13.0 |
| 7 | Ethyl-phenyl ketone | 500 | 510 | b.p. = 92° C. (5mmHg) | 14.7 | d-isomer | 25.0 | 1-ethyl-1-phenyl propargyl alcohol | (CH₃—CH₂—C(OH)(C≡CH)—C₆H₅) | +7.2° (C = 0.49) | 7.2 | −7.0° (C = 0.48) | 7.1 |
| 8 | Monobromo-methyl-phenyl ketone | 500 | 450 | b.p. = 109° C. (5mmHg) | 12.6 | d-isomer | 16.9 | 1-monobromo-methyl-1-phenyl propargyl alcohol | (Br—CH₂—C(OH)(C≡CH)—C₆H₅) | +5.2° (C = 0.19) | 6.1 | −5.3° (C = 0.19) | 6.8 |
| 9 | Trifluoro-methyl-phenyl ketone | 500 | 567 | b.p. = 93° C. (18mmHg) | 17.0 | l-isomer | 24.8 | 1-trifluoromethyl-1-phenyl propargyl alcohol | (CF₃—C(OH)(C≡CH)—C₆H₅) | +4.7° (C = 0.60) | 8.5 | −4.6° (C = 0.59) | 8.3 |
| 10 | Methyl-phenyl ketone | 500 | 505 | b.p. = 84° C. (5.5mmHg) | 19.7 | l-isomer | 35.7 | 1-methyl-1-phenyl propargyl alcohol | (CH₃—C(OH)(C≡CH)—C₆H₅) | +4.1° (C = 0.26) | 9.2 | −3.8° (C = 0.26) | 9.6 |
| 11 | 2-fluoro-benzo-phenone | 500 | 520 | b.p. = 141° C. (3mmHg) | 31.0 | l-isomer | 41.7 | 1-o-fluoro-phenyl-1-phenyl propargyl alcohol | (2-F-C₆H₄—C(OH)(C≡CH)—C₆H₅) | +61.0° (C = 0.42) | 13.8 | −59.6° (C = 0.42) | 15.2 |

TABLE 1-continued

| Example No. | Starting ketone compound | | Racemic modification | | | Deposited diastereomer | | | Optically active isomer | | | | |
|---|---|---|---|---|---|---|---|---|---|---|---|---|---|
| | | | | | | | | | | d-isomer | | l-isomer | |
| | Type | Amount used (g) | Amount obtained (g) | Boiling or melting point | Amount used (g) | Type of isomer | Amount obtained (%) | Name | Formula | $[\alpha]_D^{25}$ (methanol) | Amount obtained (g) | $[\alpha]_D^{25}$ (methanol) | Amount obtained (g) |
| 12 | 2-chloro-benzophenone | 500 | 525 | m.p. = 42° C. | 30.0 | l-isomer | 38.6 | 1-o-chlorophenyl-1-phenyl propargyl alcohol | | +132.0° (C = 0.41) | 14.5 | −129.0° (C = 0.41) | 14.7 |
| 13 | 2-bromo-benzophenone | 500 | 515 | m.p. = 53° C. | 10.6 | l-isomer | 12.3 | 1-o-bromophenyl-1-phenyl propargyl alcohol | | +108.0 (C = 0.23) | 5.3 | −114.0° (C = 0.23) | 5.2 |
| 14 | 2-methyl-benzophenone | 500 | 510 | b.p. = 127° C. (1–2mmHg) | 15.0 | l-isomer | 20.4 | 1-o-tolyl-1-phenyl propargyl alcohol | | — | — | −53.7° (C = 0.08) | 7.3 |
| 15 | 3-chloro-benzophenone | 500 | 511 | b.p. = 166° C. (5mmHg) | 30.0 | l-isomer | 39.4 | 1-m-chlorophenyl-1-phenyl propargyl alcohol | | +9.4° (C = 0.13) | 10.5 | −10.0° (C = 0.10) | 11.2 |

TABLE 1-continued

| Example No. | Starting ketone compound | | Racemic modification | | | Deposited diastereomer | | Optically active isomer | | | | | |
|---|---|---|---|---|---|---|---|---|---|---|---|---|---|
| | | | | | | | | | Name | Formula | d-isomer | | l-isomer | |
| | Type | Amount used (g) | Amount obtained (g) | Boiling or melting point | Amount used (g) | Type of isomer | Amount obtained (%) | | | $[\alpha]_D^{25}$ (methanol) | Amount obtained (g) | $[\alpha]_D^{25}$ (methanol) | Amount obtained (g) |
| 16 | 4-methyl-benzophenone | 500 | 485 | b.p. = 120° C. (1-2mmHg) | 10.0 | l-isomer | 15.6 | 1-p-tolyl-1-phenyl propargyl alcohol | [structure: p-tolyl-C(OH)(C≡CH)-phenyl] | +1.0° (C = 0.2) | 5.4 | −2.0° (C = 0.12) | 5.0 |
| 17 | 2,4-dimethyl-benzophenone | 500 | 528 | m.p. = 96° C. | 27.0 | d-isomer | 31.0 | 1-(2,4-dimethyl-phenyl)-1-phenyl propargyl alcohol | [structure: 2,4-dimethylphenyl-C(OH)(C≡CH)-phenyl] | +21° (C = 0.03) | 8.6 | −5.8° (C = 0.04) | 8.9 |
| 18 | Trichloromethyl phenyl ketone | 500 | 510 | b.p. = 138° C. (3.5mmHg) | 12.0 | d-isomer | 15.0 | 1-tri-chloromethyl-1-phenyl propargyl alcohol | [structure: CCl₃-C(OH)(C≡CH)-phenyl] | +13.8° (C = 0.175) | 5.8 | — | — |
| 19 | Dichloromethyl phenyl ketone | 500 | 520 | b.p. = 106° C. (10mmHg) | 12.0 | l-isomer | 16.7 | 1-di-chloromethyl-1-phenyl propargyl alcohol | [structure: CHCl₂-C(OH)(C≡CH)-phenyl] | — | — | −3.4° (C = 0.384) | 5.9 |
| 20 | Monochloromethyl phenyl ketone | 500 | 480 | b.p. = 98° C. (2mmHg) | 16.0 | l-isomer | 25.0 | 1-mono-chloromethyl-1-phenyl propargyl alcohol | [structure: CH₂Cl-C(OH)(C≡CH)-phenyl] | — | — | −10.5° (C = 0.182) | 7.8 |

TABLE 1-continued

| Example No. | Starting ketone compound | | Racemic modification | | | Deposited diastereomer | | Optically active isomer | | | | |
|---|---|---|---|---|---|---|---|---|---|---|---|---|
| | | | | | | | | | | d-isomer | | l-isomer |
| | Type | Amount used (g) | Amount obtained (g) | Boiling or melting point | Type of isomer | Amount obtained (%) | Name | Formula | $[\alpha]_D^{25}$ (methanol) | Amount obtained (g) | $[\alpha]_D^{25}$ (methanol) | Amount obtained (g) |
| 21 | n-propyl-thienyl ketone | 500 | 550 | b.p. = 85° C. (4mmHg) | d-isomer | 31.0 | 1-n-propyl-1-thienyl propargyl alcohol | (structure) | +3.9° (C = 0.15) | 9.7 | — | — |
| 22 | Isopropyl-thienyl ketone | 500 | 530 | b.p. = 79° (4mmHg) | d-isomer | 30.0 | 1-isopropyl-1-thienyl propargyl alcohol | (structure) | +3.2° (C = 0.18) | 9.4 | — | — |
| 23 | n-butyl-thienyl ketone | 500 | 560 | b.p. = 105° C. (10mmHg) | d-isomer | 23.8 | 1-n-butyl-1-thienyl propargyl alcohol | (structure) | +3.1° (C = 0.18) | 7.8 | — | — |
| 24 | n-amyl-thienyl ketone | 500 | 550 | b.p. = 104° C. (3mmHg) | d-isomer | 28.4 | 1-n-amyl-1-thienyl propargyl alcohol | (structure) | +5.5° (C = 0.18) | 9.8 | — | — |

We claim:

1. A method for the preparation of optically active propargyl alcohol derivatives of the formula (I):

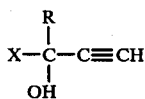

wherein X represents a member selected from the group consisting of phenyl and thienyl radicals and R represents a member selected from the group consisting of lower alkyl radicals, halogenated methyl radicals, a phenyl radical and substituted phenyl radicals each having at least one substituent selected from the group consisting of lower alkyl radicals and halogen atoms, which method comprises the steps of:

bringing a racemic modification of l- and d-propargyl alcohol derivatives of the formula (I) into contact with l-brucine in an organic solvent, whereby a mixture of diastereomers of L-brucine with an l-isomer and a d-isomer of a propargyl alcohol derivative of the formula (I) is produced and one of said diastereomers deposits from said organic solvent and the other one is dissolved in said organic solvent;

separating said deposited diastereomer from the solution containing the other diastereomer;

decomposing each of said diastereomers to dissociate l-brucine from the corresponding optically active isomer of the propargyl alcohol derivative of the formula (I) in the presence of an organic solvent which is capable of dissolving said corresponding optically active isomer and is incompatible with water by bringing each diastereomer into contact with an aqueous solution of a mineral acid; whereby the resulting optically active isomer is dissolved in the water-incompatible organic solvent and the dissociated l-brucine is dissolved in the aqueous mineral acid solution; and isolating the resultant optically active isomer from the decomposition mixture.

2. A method as claimed in claim 1, wherein said racemic modification of l- and d-propargyl alcohol derivatives of the formula (I) is prepared by reacting a ketone compound of the formula (II):

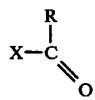

wherein X and R are the same as defined hereinbefore, with sodium acetylide in a liquid ammonia and by hydrolyzing the resultant sodium salt of the racemic modification of l- and d-propargyl alcohol derivatives of the formula (I).

3. A method as claimed in claim 1, wherein said organic solvent comprises at least one member selected from the group consisting of acetone, methyl alcohol and ethyl acetate.

4. A method as claimed in claim 1, wherein the contact of l-brucine with said racemic modification is carried out at a temperature of from 10° to 50° C.

5. A method as claimed in claim 1, wherein said diastereomer, which has deposited from said organic solvent, is dissolved in said water-incompatible organic solvent and the solution is subjected to said decomposition procedure.

6. A method as claimed in claim 1, wherein the solution containing the other diastereomer dissolved in said organic solvent is mixed with an organic solvent incompatible with water, and the mixture is subjected to said decomposition procedure.

7. A method as claimed in claim 5 or 6, wherein said water-incompatible organic solvent is selected from the group consisting of benzene, toluene and xylene.

8. A method as claimed in claim 1, wherein said contact of each diastereomer with said aqueous mineral acid solution is carried out at a temperature of from 10° to to 50° C.

9. A method as claimed in claim 1, wherein said mineral acid comprises at least one member selected from the group consisting of hydrochloric acid, sulfuric acid and nitric acid.

10. A method as claimed in claim 1, wherein the concentration of said mineral acid in said aqueous solution thereof is in the range of from 1 to 30%.

11. A method as claimed in claim 1, wherein said isolating procedure comprises separating the water-incompatible organic solvent solution phase containing the corresponding optically active isomer from the aqueous mineral acid solution phase containing the dissociated l-brucine; and eliminating said water-incompatible organic solvent from said separated organic solvent solution phase by means of evaporation.

12. A method as claimed in claim 1, wherein the lower alkyl radical represented by R in the formula (I) has from 1 to 6 carbon atoms.

13. A method as claimed in claim 1, wherein the halogenated methyl radical represented by R in the formula (I) is selected from the group consisting of chlorinated methyl radicals, fluorinated methyl radicals and brominated methyl radicals.

14. A method as claimed in claim 1, wherein the lower alkyl radicals contained in the substituted phenyl radical represented by R in the formula (I) have from 1 to 3 carbon atoms.

15. A method as claimed in claim 1, wherein the halogen atom contained in the substituted phenyl radical represented by R in the formula (I) is selected from the group consisting of chlorine, fluorine and bromine atoms.

16. A method as claimed in claim 1, wherein said optically active propargyl alcohol derivative is selected from the group consisting of
1-tert-butyl-1-phenyl propargyl alcohol,
1-tert-amyl-1-phenyl propargyl alcohol,
1-sec-butyl-1-phenyl propargyl alcohol,
1-o-tolyl-1-phenyl propargyl alcohol,
1-n-butyl-1-phenyl propargyl alcohol,
1-o-chlorophenyl-1-phenyl propargyl alcohol,
1-isopropyl-1-phenyl propargyl alcohol,
1-p-tolyl-1-phenyl propargyl alcohol,
1-n-propyl-1-phenyl propargyl alcohol,
1-o-fluorophenyl-1-phenyl propargyl alcohol,
1-ethyl-1-phenyl propargyl alcohol,
1-monobromomethyl-1-phenyl propargyl alcohol,
1-o-bromophenyl-1-phenyl propargyl alcohol,
1-trifluoromethyl-1-phenyl propargyl alcohol,
1-m-chlorophenyl-1-phenyl propargyl alcohol,
1-(2,4-dimethylphenyl)-1-phenyl propargyl alcohol,
1-methyl-1-phenyl propargyl alcohol,
1-trichloromethyl-1-phenyl propargyl alcohol,
1-dichloromethyl-1-phenyl propargyl alcohol,
1-monochloromethyl-1-phenyl propargyl alcohol,
1-n-propyl-1-thienyl propargyl alcohol,
1-isopropyl-1-thienyl propargyl alcohol,
1-n-butyl-1-thienyl propargyl alcohol and
1-n-amyl-1-thienyl propargyl alcohol.

* * * * *

UNITED STATES PATENT AND TRADEMARK OFFICE
CERTIFICATE OF CORRECTION

PATENT NO. : 4,467,102
DATED : August 21, 1984
INVENTOR(S) : Fumio TODA and Koichi TANAKA It is certified that error appears in the above—identified patent and that said Letters Patent is hereby corrected as shown below:

In the Abstract, lines 7 and 8, change "1-" to --$\ell$- --.

IN THE CLAIMS:

Claim 1, lines 12, 14, 15, 23, and 32, change "1-" to --$\ell$- --;
line 23, change "frorm" to --from--.
Claim 2, lines 2 and 9, change "1-" to --$\ell$- --.

Claim 4, line 2, change "1-" to --$\ell$- --.

Claim 11, line 6, change "1-" to --$\ell$- --.

Signed and Sealed this

Nineteenth Day of February 1985

[SEAL]

Attest:

DONALD J. QUIGG

Attesting Officer    Acting Commissioner of Patents and Trademarks